United States Patent
Bedell et al.

(10) Patent No.: US 6,803,240 B1
(45) Date of Patent: Oct. 12, 2004

(54) METHOD OF MEASURING CRYSTAL DEFECTS IN THIN SI/SIGE BILAYERS

(75) Inventors: Stephen W. Bedell, Wappingers Falls, NY (US); Keith E. Fogel, Mohegan Lake, NY (US); Devendra K. Sadana, Pleasantville, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 10/654,231

(22) Filed: Sep. 3, 2003

(51) Int. Cl.[7] .............................................. H01L 21/302
(52) U.S. Cl. ........................... 438/12; 438/14; 438/689; 438/749
(58) Field of Search ................................ 438/8, 12, 14, 438/745, 749, 700

(56) References Cited

U.S. PATENT DOCUMENTS 6,391,662 B1 * 5/2002 Mule'Stagno et al. ......... 438/8

2002/0068393 A1 * 6/2002 Fitzgerald et al. .......... 438/172
2003/0139023 A1 * 7/2003 Fogel et al. ................ 438/480
2003/0227057 A1 * 12/2003 Lochtefeld et al. ......... 257/347
2004/0000268 A1 * 1/2004 Wu et al. ..................... 117/94

FOREIGN PATENT DOCUMENTS

DE     19749962     * 11/1997

* cited by examiner

*Primary Examiner*—Savitri Mulpuri
(74) *Attorney, Agent, or Firm*—Scully, Scott, Murphy & Presser; Robert M. Trepp

(57) ABSTRACT

Described herein is a method for delineating crystalline defects in a thin Si layer over a SiGe alloy layer. The method uses a defect etchant with a high-defect selectivity in Si. The Si is etched downed to a thickness that allows the defect pits to reach the underlying SiGe layer. A second etchant, which can be the same or different from the defect etchant, is then used which attacks the SiGe layer under the pits while leaving Si intact.

20 Claims, 2 Drawing Sheets

METHOD OF MEASURING CRYSTAL DEFECTS IN THIN SI/SIGE BILAYERS

DESCRIPTION

1. Field of the Invention

The present invention relates to semiconductor device manufacturing, and more particularly to a method of determining crystal defects in a Si layer formed on a SiGe alloy layer. The method described herein is applicable to Si/SiGe bilayers formed atop bulk Si substrates as well as silicon-on-insulator (SOI)-based substrates. The method of the present invention can be used for measuring the defect density in strained Si layers grown on relaxed SiGe layers as well as any other Si/SiGe film system.

2. Background of the Invention

An important tool for the development and evaluation of high-quality Si/SiGe bilayers is a reliable method of determining the density of defects within the layers. The term "Si/SiGe bilayer" is used throughout the present application to describe a structure having a Si layer located atop a SiGe layer. In particular, accurate determination of the crystal defect density within a thin strained Si layer over a relaxed SiGe layer is important both in terms of strained Si material development as well as evaluation of existing strained Si materials. Current methods used to quantify the density of crystal defects include, for example, electron microscopy and chemical etching.

Electron microscopy can be used to measure defect densities (and character) reliably. Plan-view transmission electron microscopy (PV-TEM) can be used to measure defect densities down to approximately $10^6$ to $10^5$ defects per square centimeter. Because of the small imaging area, however, lower defect densities cannot be measured reliably using this technique. Other prohibitive elements of PV-TEM analysis are the long and cumbersome sample preparation, the need for expensive electron microscopic equipment and qualified personnel to operate the tool.

In chemical defect etching, the surface of the crystal is continually removed by an etchant that has a higher etch rate at, or near, the crystal defects compared to non-defective regions. The result is the development of surface steps or etch pits that can be examined under a microscope to determine the defect density. This prior art method relies on 1) a difference in the etch rate of defective versus non-defective regions, and 2) removal of enough material to create surface steps with sufficient contrast to be observed under a microscope. Items 1) and 2) mentioned above are related in the sense that if the etch rate difference is large; less material can be removed to obtain the same surface contrast.

A prior art chemical defect etching method that is used to evaluate silicon-on-insulator (SOI) substrates is one that uses a dilute Secco (F. Secco d'Aragona, J. Electrochem. Soc., vol. 119 no. 7 1972 p.948) defect etchant—the Secco etchant is a mixture of potassium dichromate, hydrofluoric (HF) acid and distilled water. The defect etchant is used to thin the SOI layer down to a few hundred angstroms thick (from 500 Å or thicker) and create surface pits that reach the buried oxide layer. Subsequent soaking in hydrofluoric acid leaves the SOI layer intact, but goes through the etch pits and aggressively attacks the buried oxide in that region. The result is a method which 'decorates' the etch pits by undercutting the buried oxide enough to be visible with a microscope.

The problem with chemical defect etching of SiGe-based materials is that the defect etch selectivity is very poor (defect etch rate vs. material etch rate) for most available etchants such as Secco, Shimmel (D. G. Shimmel, J. Electrochem. Soc., vol. 126 no. 3 1979 p. 479), etc. Most oxidation-based etchants etch SiGe much faster than Si, and the etch rate increases with increasing Ge content. Because of this reduced defect selectivity within SiGe, the prior art defect etching techniques are unreliable, especially for the case of ultra-thin SiGe layers (on the order of about 100 nm or less).

In view of the problems associated with prior art techniques that employ electron microscopy or the lack of reliable chemical etching techniques to determine the defect density in a Si/SiGe bilayer, there is a need for providing a new and improved method for delineating crystal defects in Si/SiGe bilayers.

SUMMARY OF THE INVENTION

The present invention relates to a method for delineating crystal defects in a Si layer formed over a SiGe alloy layer. The inventive method first employs a defect etchant with a high-defect selectivity in Si. The Si is etched down to a thickness that allows for the formation of defect pits, which contact the underlying SiGe layer. A second etchant, which can be the same or different from the defect etchant, is then employed which attacks the SiGe layer under the defect pits while leaving the overlying Si layer intact. In some embodiments, the first defect etchant itself can act simultaneously as the SiGe decoration as well. The method of the present invention can be used to measure crystalline defect densities of arbitrary magnitude quantitatively and accurately.

The method of the present invention can be used to measure crystal defects in strained Si layers grown on relaxed SiGe layers as well as any other Si/SiGe film system. The Si/SiGe bilayer may be located atop a Si substrate (or wafer) or a silicon-on-insulator (SOI)-based substrate. The method can be used to measure crystalline defects in a Si/SiGe bilayer in which the Si layer is a strained layer having a thickness on the order of about 100 nm or less and the SiGe layer is a relaxed layer having a thickness of from about 10000 nm or less. The method of the present invention works with other thickness ranges besides the aforementioned ranges.

In broad terms, the present invention provides a method for delineating, i.e., determining, the crystal defects in a Si layer located atop a SiGe layer which comprises the steps of:

first etching a structure including a Si layer located on a SiGe alloy layer with a defect etchant that is defect selective in Si to form at least one pit defect in the Si layer that is in contact with the SiGe alloy layer, and second etching the structure containing the at least one pit defect with the same or different etchant as the first etching such that the second etching undercuts the SiGe layer beneath the at least one pit defect.

In accordance with the present invention, the first etching step uses a defect etchant that etches defects, such as dislocation and stacking faults, very quickly in Si, whereas the non-defective Si etches more slowly.

In the embodiment in which the same etchant is used in the second etching step, the SiGe layer is quickly attacked and undercutting occurs. This embodiment of the present invention may be referred to as a "self-decorating" since the etchant used in forming the pit defect in the Si layer is also used to undercut the SiGe layer.

In another embodiment of the present invention, the second etching step is performed utilizing an etchant that is different from the defect etchant used in forming the pit defects in the Si layer. In this embodiment of the present invention, an etchant that etches SiGe faster than Si is employed. That is, an etchant that is highly selective to Si is employed in this embodiment of the present invention.

After performing the first and second etching steps, the etched structure is scanned under an optical microscope to identify the region (or regions) where the defect pits have been undercut. The number of etch pits that have been undercut are then determined within a given region and the defect density is reported as the number of these undercut defects divided by the area, in $cm^2$, of the analyzed region.

DETAILED DESCRIPTION OF THE INVENTION

Figure 1:
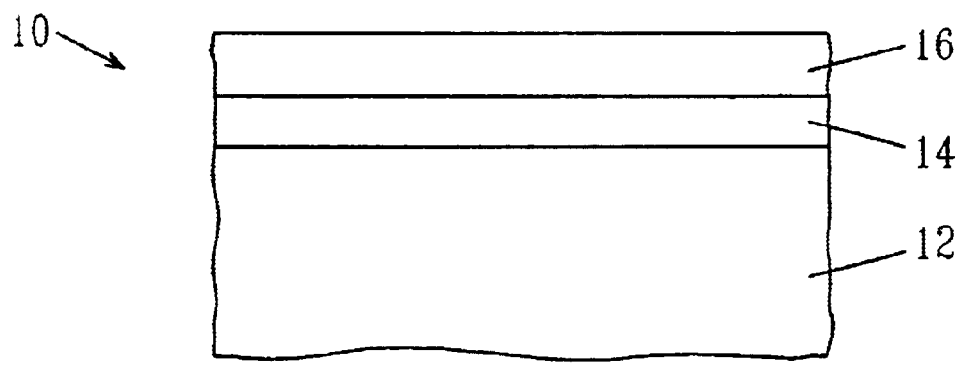
FIG. 1 is a pictorial representation showing an initial structure that can be employed in the present invention.

The present invention, which provides a method for delineating the crystal defects in a Si/SiGe bilayer, will now be described in greater detail with reference to the drawings that accompany the present application. In the drawings, like and corresponding elements are referred to by like reference numerals.

Reference is first made to the initial structure shown in FIG. 1 of the present application. The initial structure 10 includes at least a Si layer 16 located atop a SiGe layer 14. The initial structure 10 also includes a substrate 12 that is located beneath the SiGe layer 14. The substrate 12 may include a bulk Si substrate or any other semiconductor substrate as well as the buried insulating region and bottom semiconductor layer of a silicon-on-insulator (SOI) substrate; the top SOI layer of the SOI substrate has been used in formation of the SiGe layer.

The initial structure 10 shown in FIG. 1 is formed utilizing methods well known to those skilled in the art. For example, the initial structure 10 can be formed by first growing a SiGe layer 14 atop a substrate 12 and then growing a Si layer 16 atop the SiGe layer 14. In such an embodiment, the SiGe layer 14 may be grown utilizing an epitaxial growth method including, for example, low-pressure chemical vapor deposition (LCVD), ultra-high vacuum chemical vapor deposition (UHVCVD), atmospheric pressure chemical vapor deposition (APCVD), molecular beam epitaxy (MBE) or plasma-enhanced chemical vapor deposition (PECVD).

The thickness of the SiGe layer 14 may vary depending upon the epitaxial growth method used in forming the same. Typically, however, the SiGe layer 14 has a thickness of from about 10 to about 10000 nm, with a thickness of from about 10 to about 5000 nm being more highly preferred. The SiGe layer 14 may be a non-relaxed layer, or if the SiGe layer 14 is thick (on the order of about 1 to about 10 micrometers), the SiGe layer may be a relaxed layer.

The SiGe alloy layer 14 includes SiGe materials that comprise up to 99.99 atomic percent Ge. Preferably, the SiGe alloy layer of the present invention has a Ge content of from about 5 to about 99.9 atomic percent, with a Ge content of from about 10 to about 50 atomic percent being more highly preferred.

The Si layer 16 is formed atop the SiGe layer 14 utilizing a conventional epitaxial growth method wherein a Si-containing gas such as a silane or dichlorosilane is used as the source for growing Si. The thickness of the epi-Si layer, i.e., layer 16, may vary, but typically, the Si layer 16 has a thickness of from about 1 to about 100 nm, with a thickness of from about 1 to about 50 nm being more highly preferred. In instances in which the SiGe alloy layer is relaxed, the Si layer 16 is a tensile stained layer.

The structure shown in FIG. 1 may also be formed utilizing the method disclosed, for example, in co-pending and co-assigned U.S. patent application Ser. No. 10/055, 138, filed Jan. 23, 2002, entitled "Method of Creating High-Quality Relaxed SiGe-on-Insulator for Strained Si CMOS Applications", co-pending and co-assigned U.S. patent application Ser. No. 10/196,611, filed Jul. 16, 2002, entitled "Use of Hydrogen Implantation to Improve Material Properties of Silicon-Germanium-On-Insulator Material Made by Thermal Diffusion" as well as co-pending and co-assigned U.S. patent application Ser. No. 10/448,948, filed May 30, 2003, entitled "High-Quality SGOI By Oxidation Near The Alloy Melting Temperature". The entire contents of each of the aforementioned U.S. patent applications are incorporated herein by reference. It is noted that in these applications a thermal mixing step is employed in forming a relaxed SiGe layer over a buried insulator layer of an SOI substrate.

In addition to the specific methods mentioned above, the initial structure shown in FIG. 1 can be formed utilizing any other method that is capable of forming a Si/SiGe bilayer structure. As stated above, the Si layer can be strained or unstrained, and the SiGe layer may be relaxed or non-relaxed. The strained Si/relaxed SiGe bilayer is a heterostructure that is capable of achieving high channel electron mobility.

The structure including the Si/SiGe bilayer is then subjected to a first etching step. The first etching step employed in the present invention includes the use of a defect etchant that has a very high defect selectivity in Si. The defect etchants employed in the present invention typically include an oxidizing agent and an oxide etchant such as HF acid. Illustrative examples of defect etchants that can be employed in the present invention include, but are not limited to: a mixture of 2 parts HF and 1 part potassium dichromate solution (0.15 M) (Secco) that may be optionally diluted with water to control the etch rate, or 2 parts HF and 1 part chromium trioxide (1 M) optionally diluted with water (Shimmel), or any other chemical mixture that etches defective crystalline Si regions at a higher rate than non-defective Si.

Of the various defect etchants mentioned above, a 2:1 HF:potassium dichromate (0.15 M) solution diluted with an equal volume of water is highly preferred. Typically, six parts of deionized water is employed. The defect etchants employed in this step of the present invention etch the dislocation and stacking fault defects at a much faster rate than non-defective Si.

In accordance with the present invention, the first etching step is conducted at room temperature or a temperature slightly elevated from room temperature (30° C. or less) for a time period of from about 10 to about 1000 seconds. The time period is a function of Si thickness as well as the etch rate of the defect etchant and therefore it may vary somewhat from the range provided above.

Figure 2:
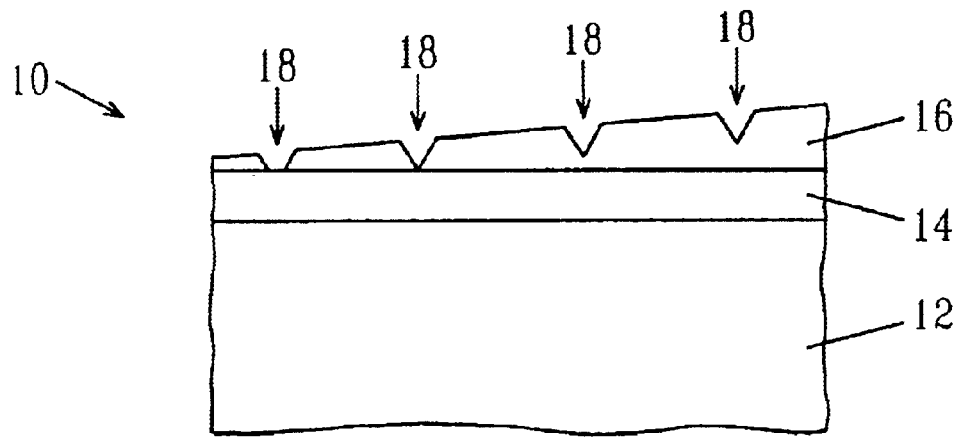
FIG. 2 is a pictorial representation showing a first step of the present invention for determining crystal defect density in the initial structure shown in FIG. 1.

The resultant structure that is formed after the first etching step of the present invention has been performed is shown, for example, in FIG. 2. Note that in FIG. 2 the sample was etched using a dilute 2:1 HF-potassium dichromate solution in a linear 'wedge' profile.

As shown in FIG. 2, the first etching step of the present invention forms a plurality of defect pits 18 in the Si layer 16. Depending on the thickness of the Si layer 16, some of the defect pits 18 extend down to the SiGe layer 14. Thus, some of the pit defects 18 are in contact with the underlying SiGe layer 14.

A second etching step is now performed which provides an undercut in the SiGe layer 14 underneath the defect pits 18 that are contact with the SiGe layer 14. The resultant structure after performing the second etching step is shown, for example, in FIG. 3. In this drawing, reference numeral 22 denotes the undercut region.

The second etching step may include a "self-decorating" step wherein the same etchant as used in the first etching step is employed. When the defect etchant at the pit defects reaches the underlying SiGe, the SiGe is quickly attacked and undercutting occurs. This embodiment of the present invention is particularly useful when the Si layer is thick (greater than 150 Å).

For thinner Si layers (on the order of about 150 Å or less), an alternative approach is employed to provide undercuts in the SiGe layer beneath the pit defects that are in contact with the SiGe layer. In this second embodiment of the present invention, a different chemical etchant as compared to the defect etchant employed above is used to provide the undercutting. In particular, the etchant used in the second embodiment of the present invention is any etchant that etches SiGe at a faster rate than Si.

Illustrative examples of etchants that can be employed in the second embodiment of the present invention include, but are not limited to: a HF/$H_2O_2$/acetic acid (HHA) mixture (ratio 1:2:3, respectively), or 100:1 Nitric acid:HF mixture. Of the various etchants mentioned above, it is highly preferred to use an HHA mixture since the etch rate of SiGe in this etchant is several orders of magnitude greater than Si while the absolute etch rate of silicon is very low (<1 Å/min.). This allows the HHA mixture to be used as a decoration etch; it leaves the Si intact while aggressively undercutting exposed SiGe.

In accordance with the present invention, the second etching step is conducted at room temperature or a temperature slightly elevated from room temperature (30° C. or less) for a time period of from about 1 to about 1000 seconds. The time period is a function of the etch rate of the etchant used in this step of the present invention.

In some instances, a rinsing step, and an optional drying step, may be performed between the first and second etching steps. When the rinsing step is employed, the rinsing solution is typically distilled or deionized water. Other types of rinsing solutions that can be employed in the present invention include, but are not limited to: alkanes such as hexane or heptane, ketones or alcohols. Drying may be performed in air, in an inert ambient, in an oven, or in vacuum.

In either of the two embodiments mentioned above, it is difficult, in practice, to stop the etching process at precisely the optimum Si thickness. One method of etching, which can be employed herein, that guarantees a region with the optimum etched Si thickness is to perform a "graded etch". Specifically, the structure to be etched is first submerged into an etchant bath that includes the defect etchant slowly at a rate that results in the Si being completely etched (down to SiGe) at the bottom of the sample, while the full Si thickness remains at the top.

Figure 3:
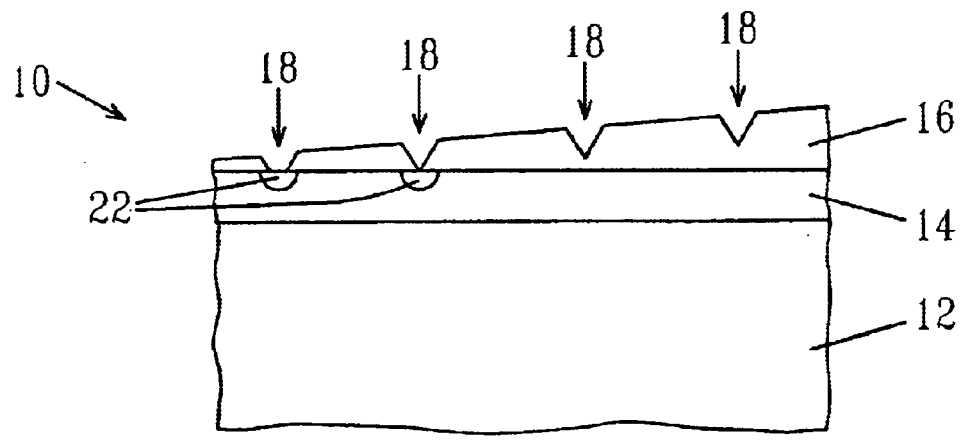
FIG. 3 is a pictorial representation showing a second step of the present invention for determining crystal defect density from the structure shown in FIG. 2.

The structures shown in FIGS. 2 and 3 have been etched using the graded method. As such, the portion of the structure that is submerged first can be referred to as the "bottom" of the structure and the other portion that is submerged last may be referred to as the "top" of the structure. The terms "top" and "bottom" are relative to which end of the structure is first submerged into the etchant bath. By using this grading etching method, the top Si thickness will decrease approximately linearly from the top to the bottom of the structure. The submersion of the sample into the etch solution can be performed either manually (by hand) or using an automated apparatus for improved control of the graded profile.

The etched structure shown in FIG. 3 is then scanned under an optical microscope (or even an atomic force microscope) to identify the region (or regions) where the defect pits have been undercut. The number of etch pits that have been undercut are then determined within a given region and the defect density is reported as the number of these undercut defects divided by the area, in $cm^2$, of the analyzed region.

Figure 4:
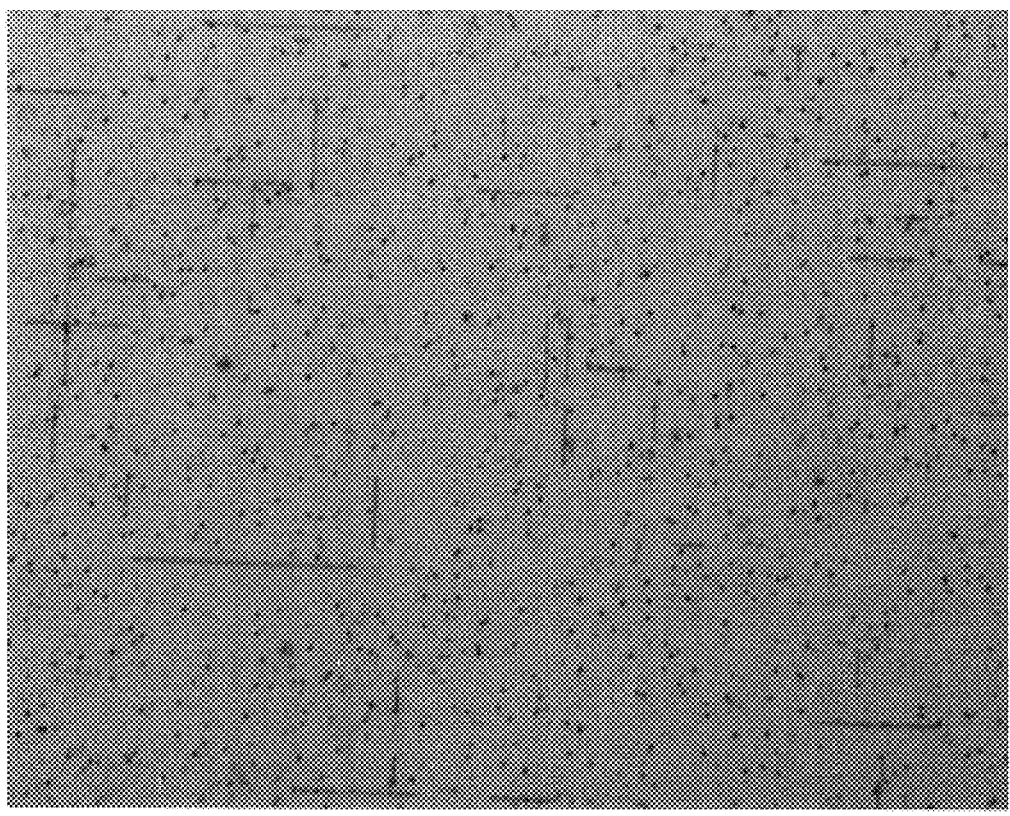
FIG. 4 is an optical micrograph (Nomarski contrast) of a 150 Å Si/350 Å SiGe/1400 Å $SiO_2$/Si substrate structure after defect etching using the method of the present invention. The image width is 86 μm.

FIG. 4 is an actual optical micrograph (Nomarski contrast) of a 150 Å Si/350 Å SiGe/1400 Å $SiO_2$/Si substrate structure after defect etching using the method of the present invention. The image width is 86 µm. The image clearly shows the delineation of etch pits as well as planar defects such as stacking faults. The image was taken at a region near the Si/SiGe interface in the graded etch profile.

While the present invention has been particularly shown and described with respect to preferred embodiments thereof, it will be understood by those skilled in the art that the foregoing and other changes in forms and details may be made without departing from the scope spirit of the present invention. It is therefore intended that the present invention not be limited to the exact forms and details described and illustrated, but fall within the scope of the appended claims.

What is claimed is:

1. A method for delineating crystal defects in a Si/SiGe bilayer structure comprising the steps of:
   first etching a structure including a Si layer located on a SiGe alloy layer with a defect etchant that is defect selective in Si to form at least one pit defect in the Si layer that is in contact with the SiGe alloy layer;
   second etching the structure containing the at least one pit defect with the same or different etchant as the first etching such that the second etching undercuts the SiGe layer beneath the at least one pit defect; and
   identifying a region where at least pit defect in Si layer has been undercut and calculating the defect density in Si layer based on the total undercut pit defects divided by area.

2. The method of claim 1 wherein the Si layer is formed by epitaxy, and the SiGe alloy layer is formed by epitaxy.

3. The method of claim 1 wherein the Si layer is a strained layer and the SiGe alloy layer is a relaxed layer.

4. The method of claim 3 wherein the strained layer has a thickness of about 100 nm or less and the relaxed layer has a thickness of from about 10000 nm or less.

5. The method of claim 1 wherein a thermal mixing process is employed in forming said SiGe alloy layer atop a buried insulator layer of a silicon-on-insulator substrate.

6. The method of claim 1 wherein the SiGe alloy layer comprises up to 99.99 atomic percent Ge.

7. The method of claim 1 wherein the SiGe alloy layer is formed atop a substrate.

8. The method of claim 7 wherein the substrate is bulk Si or a silicon-on-insulator-based substrate.

9. The method of claim 1 wherein the defect etchant comprises a mixture of HF and potassium dichromate, a mixture of HF, potassium dichromate and distilled water, a mixture of HF and chromium trioxide, or a mixture of HF, chromium trioxide and distilled water.

10. The method of claim 1 wherein the defect etchant comprises 2 parts HF and 1 part of a 0.15 M potassium dichromate solution and 6 parts deionized water.

11. The method of claim 1 wherein the defect etchant etches dislocation and stacking fault defects at a much faster rate than non-defective Si.

12. The method of claim 1 wherein the first etching is performed using a graded etching process.

13. The method of claim 1 wherein the second etching employs the same etchant as the first etching.

14. The method of claim 1 wherein the defect etchant and the etchant in the second etch are both comprised of 2 parts HF and 1 part of a potassium dichromate solution and 6 parts deionized water.

15. The method of claim 1 wherein the second etching is performed using a different etchant as the defect etchant, said different etchant etches SiGe at a faster rate than Si.

16. The method of claim 15 wherein the different etchant comprises $HF/H_2O_2$/acetic acid or Nitric/HF.

17. The method of claim 15 wherein the different etchant comprises 1 part HF/2 parts $H_2O_2$/ and 3 parts acetic acid.

18. The method of claim 1 further comprising a rinsing step between said first and second etching steps.

19. The method of claim 1 identifying comprises scanning the first and second etched structure under a microscope.

20. A method of measuring the crystal defects in a Si/SiGe bilayer structure comprising:

first etching a structure including a Si layer located on a SiGe alloy layer with a defect etchant that is defect selective in Si to form at least one pit defect in the Si layer that is in contact with the SiGe alloy layer;

second etching the structure containing the at least one pit defect with the same or different etchant as the first etching such that the second etching undercuts the SiGe layer beneath the at least one pit defect; and scanning the etched structure under a microscope to identify a region where the at least one pit defect is undercut and calculating the number of defects in the Si layer in terms of defect density.

* * * * *